United States Patent
Caldeira et al.

(10) Patent No.: US 10,674,685 B2
(45) Date of Patent: Jun. 9, 2020

(54) SYSTEMS AND METHODS FOR SELECTIVE POLLINATION

(71) Applicant: Elwha LLC, Bellevue, WA (US)

(72) Inventors: Kenneth G. Caldeira, Redwood City, CA (US); Alistair K. Chan, Bainbridge Island, WA (US); Roderick A. Hyde, Redmond, WA (US); Jordin T. Kare, San Jose, CA (US); Max N. Mankin, Cambridge, MA (US); Tony S. Pan, Bellevue, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 792 days.

(21) Appl. No.: 14/730,686

(22) Filed: Jun. 4, 2015

(65) Prior Publication Data
US 2016/0353661 A1 Dec. 8, 2016

(51) Int. Cl.
*A01H 1/02* (2006.01)

(52) U.S. Cl.
CPC .................. *A01H 1/02* (2013.01)

(58) Field of Classification Search
CPC .................. A01H 1/02; A01H 1/025
USPC .................. 47/1.41
See application file for complete search history.

(56) References Cited

U.S. PATENT DOCUMENTS

| | | | | |
|---|---|---|---|---|
| 6,357,171 B1 * | 3/2002 | Harper | .................. | A01H 1/025 449/1 |
| 8,391,550 B2 * | 3/2013 | Pachys | .................. | G01N 23/046 382/103 |
| 2001/0036295 A1 * | 11/2001 | Hendrickson | ......... | G01J 3/2803 382/110 |
| 2005/0126144 A1 * | 6/2005 | Koselka | .................. | A01D 46/30 56/10.2 R |
| 2013/0305600 A1 * | 11/2013 | Whaley | .................. | A01H 1/025 47/1.41 |
| 2016/0260207 A1 * | 9/2016 | Fryshman | ............. | G06T 7/0008 |

FOREIGN PATENT DOCUMENTS

| | | |
|---|---|---|
| CN | 203167756 U | 9/2013 |
| JP | 2011-200196 A | 10/2011 |

OTHER PUBLICATIONS

Pantech Solutions. (Aug. 12, 2014). Robot Bees. Retrieved from Pantech Solutions: https://www.pantechsolutions.net/blog/robot-bees/.*
PCT International Search Report; International App No. PCT/US2016/035241; dated Sep. 13, 2016; pp. 1-3
(Continued)

*Primary Examiner* — Monica L Williams
*Assistant Examiner* — Aaron M Rodziwicz
(74) *Attorney, Agent, or Firm* — Foley & Lardner LLP

(57) ABSTRACT

A method of pollinating a plant includes receiving, with a processing circuit, plant data regarding a plant having flowers, and controlling, by the processing circuit, operation of an robotic device to selectively pollinate a portion of the plurality of flowers based on the plant data. The robotic device includes sensors configured to acquire plant data, a pollination device configured to pollinate flowers of a plant, a collection device configured to collect pollen, and a pollination prevention device configured prevent a flower from being pollinated.

10 Claims, 7 Drawing Sheets

(56) References Cited

OTHER PUBLICATIONS

Insectbot Kit, http://www.dfrobot.com/index.php?route=product/product&product_id=1055, retrieved on Jul. 29, 2015, 13 pages.
Robobees, http://robobees.seas.harvard.edu/, retrieved on Jul. 29, 2015, 2 pages.

* cited by examiner ly SYSTEMS AND METHODS FOR SELECTIVE POLLINATION

BACKGROUND

Plants reproduce via pollination, when genetic material is transferred amongst plants, flowers of plants, or within a flower by itself. Pollination may be managed by manually transporting pollen, or by raising bees that pollinate plants.

SUMMARY

One embodiment relates to a method of selectively preventing pollination of plants. The method includes a receiving step in which a processing circuit receives plant data regarding a flower of a plant. The method also includes a controlling step in which a processing circuit controls operation of a robotic device to selectively perform a pollination prevention process to at least temporarily prevent pollination of the flower based on the plant data.

Another embodiment relates to a method of collecting pollen from plants. The method includes a receiving step in which a processing circuit receives plant data regarding a flower of a plant. The method also includes a controlling step in which the processing circuit controls operation of a robotic device to collect pollen from the flower based on the plant data.

Another embodiment relates to a method of monitoring pollinated plants. The method includes an acquiring step in which a robotic device acquires plant data from a flower of a plant. The method also includes a determining step in which a processing circuit of the robotic device determines whether the flower has been pollinated based on the plant data.

Another embodiment relates to a method of pollinating a plant. The method includes a receiving step, in which a processing circuit receives plant data regarding a plant having a plurality of flowers. The method also includes a controlling step, wherein the processing circuit controls operation of a robotic device to selectively pollinate a portion of the plurality of flowers of the plant based on the plant data.

Another embodiment relates to a system for selectively pollinating plants. The system includes a pollination prevention device configured to at least temporarily prevent pollination of a flower of a plant. The system also includes a processing circuit configured to control operation of the pollination prevention device based on plant data.

Another embodiment relates to a robotic device for collecting pollen from plants. The robotic device includes a collection device, a sensor configured to acquire plant data regarding a plant, and a processing circuit configured to control operation of the collection device to collect pollen from a flower of the plant based on the plant data.

Another embodiment relates to a robotic device for monitoring pollinated plants. The robotic device includes a sensor configured to acquire plant data regarding a flower of a plant. The robotic device also includes a processing circuit configured to control operation of the sensor and determine whether the flower has been pollinated based on the plant data.

Another embodiment relates to a robotic device for pollinating a plant. The robotic device includes a pollination device configured to deliver pollen to a plurality of flowers of a plant. The robotic device also includes a sensor configured to collect plant data regarding the plurality of flowers. The robotic device also includes a processing circuit configured to control operation of the pollination device based on the plant data.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
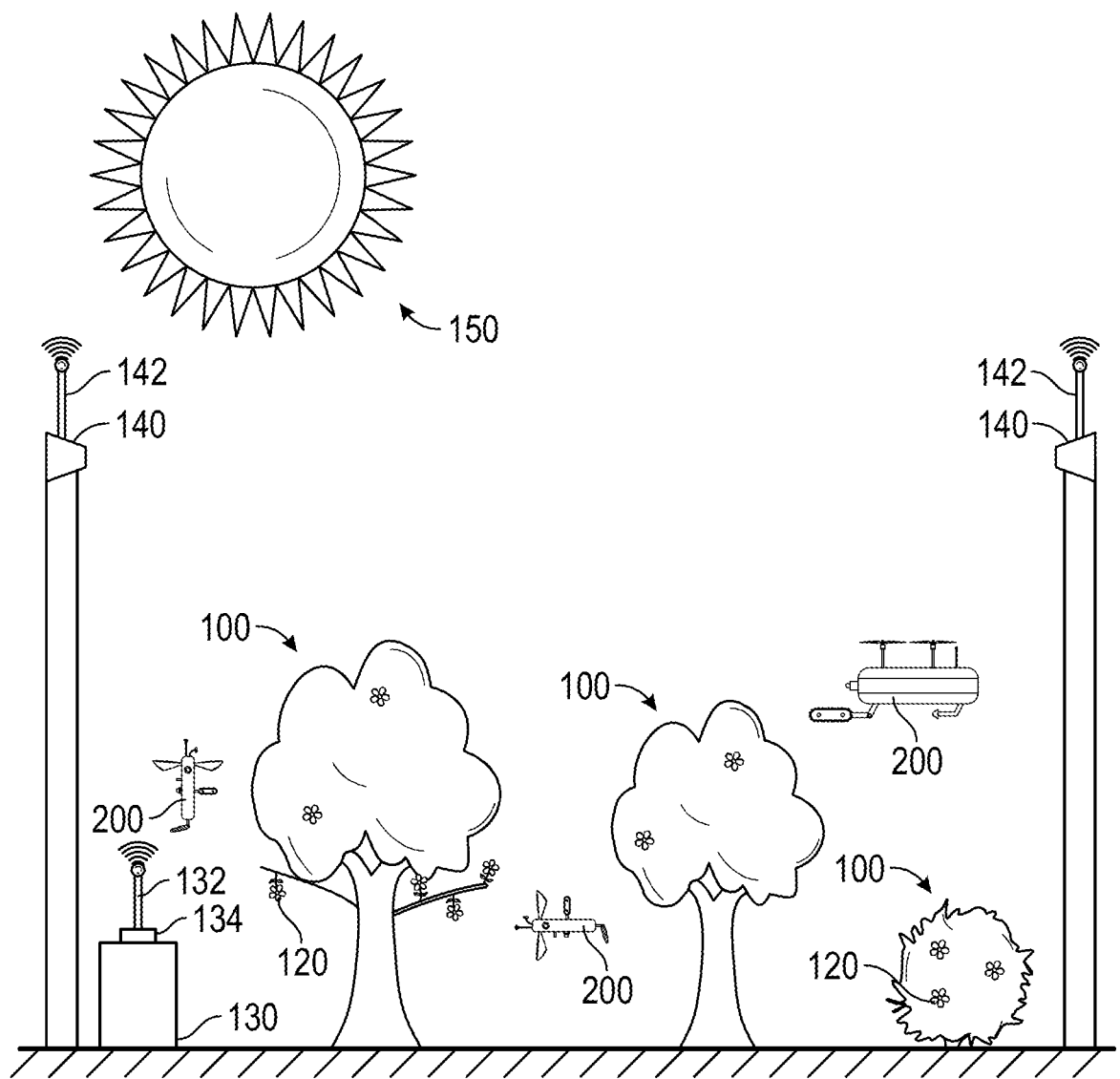
FIG. 1 is a schematic illustration of robotic devices and a plurality of plants according to one embodiment.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

When describing an apparatus, method, or system regarding a plurality of items, such as a plurality of flowers, any references to the items, such as through the terms 'the,' 'each,' 'one of,' and other such terms, are generally not meant to be limiting. Rather, in general, any data regarding, analysis of, methods and steps performed on, or other matters concerning the plurality could potentially apply to any subset of the plurality, including but not limited to one item or every item. Additionally, in general, embodiments of the invention as applied to pollinating a plant may also be applied to pollinating any of a plurality of flowers of a plant.

Referring to the figures generally, various embodiments disclosed herein relate to apparatuses, methods, and systems of pollinating plants with robotic devices. In one embodiment, a robotic device has a collection device with a moist surface configured to collect pollen from a flower of a plant. The robotic device collects pollen from a flower. The robotic device also includes a sensor configured to collect plant data regarding a flower of the plant, as well as a processing circuit configured to control operation of the robotic device based on the plant data. The processing circuit uses the plant data to determine whether a flower has been pollinated. The robotic device also has a pollination device configured to deliver pollen to a flower of the plant. The processing circuit determines whether a flower has been pollinated, then delivers pollen to the flower if it has not been pollinated.

In various embodiments, an environment may be defined as any region surrounding plants to be pollinated. The environment may be expanded or contracted as desired. The environment need not be uniform, but may have sub-regions that depart from an otherwise uniform profile. In some embodiments, to facilitate navigation and calculation of distances, sizes, shapes, and other spatial elements within the environment, any appropriate coordinate system may be defined relative to the environment, including but not limited to a Cartesian x-y-z coordinate system based on linear distances relative to an origin position, or a cylindrical r-z-θ coordinate system based on radial distances, vertical distances, and angles swept relative to an origin position.

In the environment, a local range may be defined as the region representing the maximum distance the pollination device can reach, given that the robotic device has a relatively fixed position. Similarly, a global range may be defined as the region within the environment that a pollination device may reach, given that the robotic device including the pollination device does not have a fixed position.

Referring to FIG. 1, robotic devices 200 may be used to pollinate flowers 120 of plants 100 of various sizes, shapes, and other features. In some embodiments, robotic devices 200 may communicate (e.g., via wireless optical, microwave, or ultrasonic signals) with each other, and/or with central computer 130, to determine which plants 100 in a common environment each of the robotic devices 200 will pollinate. In some embodiments, first robotic device 200 pollinates all flowers within a first global range, while second robotic device 200 pollinates all flowers within a second global range, and third robotic device 200 prevents pollination of all flowers within a third global range. While FIG. 1 illustrates robotic devices 200 as being airborne, in various embodiments, robotic devices 200 may be provided as being non-airborne (see, e.g., robotic devices 200 shown in FIGS. 2C-2D, etc.).

Robotic devices 200 may communicate with sensors 140 that provide information regarding the environment surrounding the plants 100 to be pollinated. Sensors 140 may be light sensors sensitive to a particular light source, such as sun 150, or to the intensity of light passing to a particular position in the environment. Sensors 140 may also be temperature sensors that are sensitive to the ambient temperature at a particular position in the environment. Sensors 140 may also be humidity sensors sensitive to the moisture content of a particular position in the environment. Sensors 140 may also be air flow sensors sensitive to the wind speed or direction at a particular position in the environment. Sensors 140 may also be chemical, image, or other sensors configured to detect the presence of pollen (e.g., pollen 450 shown in FIG. 4C) in the environment.

Figure 2A:
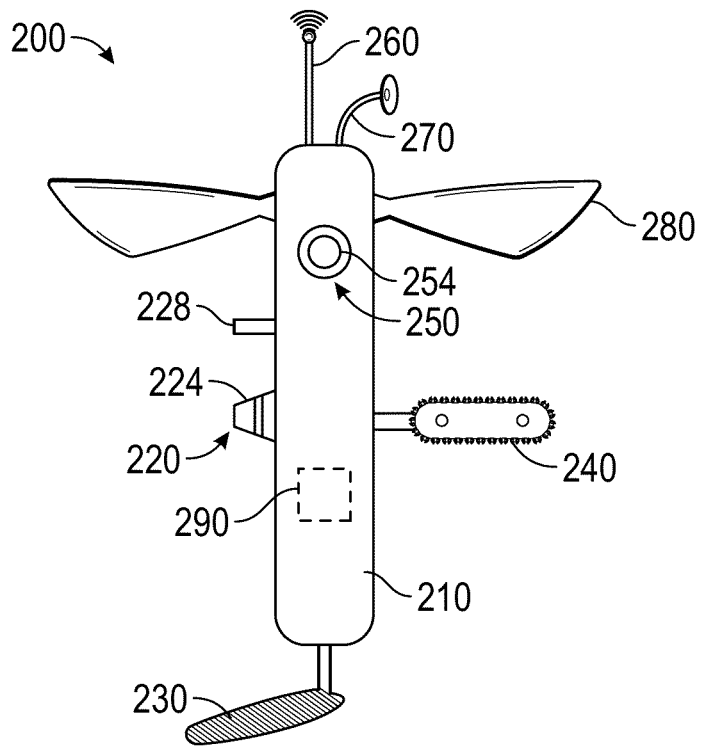
FIGS. 2A and 2B are schematic illustrations of the robotic devices of FIG. 1 shown in greater detail according to various embodiments.
Figure 2B:
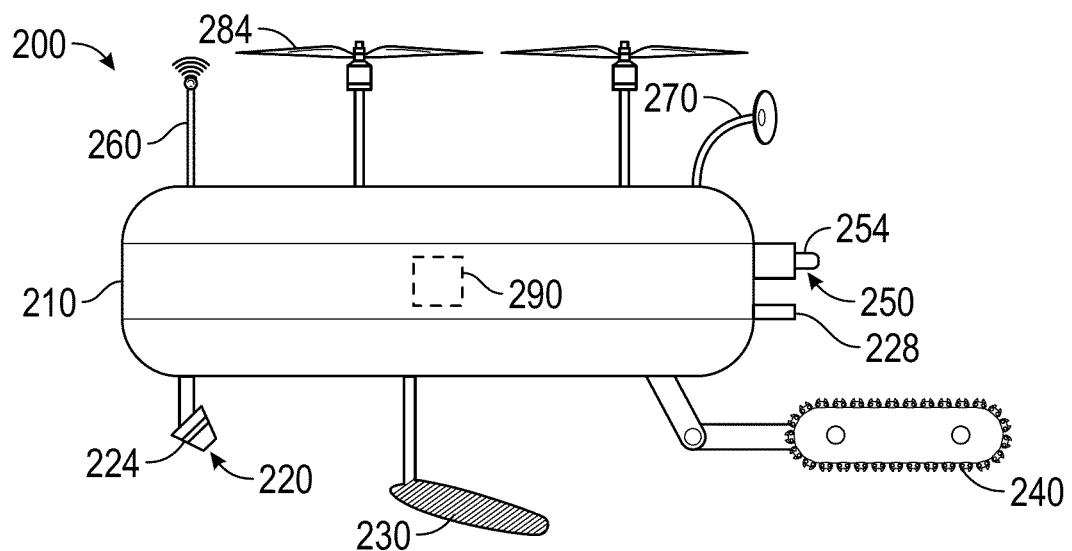

Referring to FIGS. 2A and 2B, robotic devices 200 may include chassis 210 (e.g., a body, a main portion, etc.), pollination device 220, collection device 230, and pollination prevention device 240. Robotic devices 200 may also include a processing circuit (e.g., processing circuit 310 shown in FIG. 3) configured to control operation of pollination device 220, collection device 230, and pollination prevention device 240.

In some embodiments, pollination device 220 includes nozzle 224 for providing pollen 450. In some embodiments, pollination device 220 may store pollen 450 as pellets, and provide them one at a time. Processing circuit 310 may be configured to control operation of a drive for providing pollen 450. Robotic device 200 may include stores for storing multiple pollens 450 of multiple pollen types.

In some embodiments, collection device 230 includes a moist surface. Robotic device 200 may include a tank for fluid to be passed to the surface of collection device 230. The fluid may have adhesive properties.

In some embodiments, collection device 230 includes an adhesive surface. The adhesive surface may have glue or other adhesives applied to it. The adhesive surface may be movable (e.g., via a reel) to periodically expose new surface and to de-expose old surface. The adhesive surface may include fibers or other small protrusions to increase the surface area of the surface that provides adhesion in order to adhere to pollen 450.

In some embodiments, robotic device 200 includes sensor 250 configured to acquire plant data regarding plant 100. Sensor 250 may be attached to chassis 210, or may be located within chassis 210. As shown in FIG. 2A, sensor 250 includes camera 254 located on chassis 210 of robotic device 200. Camera 254 may capture still images or videos of flower 120, or may provide a real-time stream of the image of flower 120. Camera 254 may be configured to capture visual information about flower 120 in the visible spectrum, or the infrared spectrum, or any other portion of the electromagnetic spectrum. In some embodiments, sensor 250 is or includes at least one of camera 254, a laser distance sensor, an infrared distance sensor, and an ultrasonic distance sensor.

As shown in FIG. 1, sensor 140 is located remote from robotic device 200. Sensor 140 may be placed in a position with optimal visual coverage of flower 120. Sensor 140 may be placed where it has a clear view of multiple flowers 120. Sensor 140 may communicate directly or indirectly with robotic device 200. Sensor 140 may be configured to coordinate plant data with plant data sensed by sensor 254.

In some embodiments, robotic device 200 includes communication device 260. Communication device 260 may transmit and receive information between processing circuit 310 and a variety of sources, and may be configured to receive and transmit signals (wirelessly or via cables or fibers) throughout the electromagnetic spectrum, including but not limited to infrared, radio frequency, and microwave signals, and electronic communication protocols such as wireless internet, wired internet, Bluetooth, and near field technologies. In some embodiments, robotic device 200 includes sensor 250, and communication device 260 may transmit and receive information to and from sensor 250 and processing circuit 310.

In some embodiments, sensor 140 may be connected to sensor communication device 142 (see FIG. 1) that communicates with communication device 260 onboard robotic device 200. Sensor communication device 142 may also communicate indirectly with communication device 260 onboard robotic device 200 via a central communication hub, such as central communication hub 134 communicably connected to central communication device 132, and may communicate using any communication protocol, including but not limited to the internet, a local intranet or other local communication protocol, radio, and Bluetooth or other short range communication protocols.

In some embodiments, robotic device 200 includes detection device 270 configured to detect at least one of a previously emplaced pollen on the stigma, entry of a pollen into the stigma (e.g. pollen 450 and stigma 410 shown in FIG. 4C), and a pollen tube, in order to determine if pollination has occurred. For example, in some embodiments, detection device 270 includes a camera configured to capture images of plants 100 and portions of plants 100, and transmit the images to processing circuit 310; processing circuit 310 then compares the images to other previously stored images in order to determine if the images captured by the camera match the stored images. In some embodiments, a user may visually inspect images captured by the camera to determine whether pollination has occurred. In some embodiments, detection device 270 includes an ultrasonic sensor to apply ultrasound to one or more locations of a plant and detect transmitted or scattered ultrasonic signals (e.g., to probe internal structures of the plant or flower). Similarly, detection device 270 and processing circuit 310 may be configured to analyze images (e.g., visual, thermal, ultrasonic) of plants 100 to determine if fertilization has occurred (e.g. whether embryonic development has started), or may allow a user to visually inspect images of plants 100 to determine if fertilization has occurred. In some embodiments, detective device 270 includes a temperature sensor such as a thermometer or a thermal imager to determine the temperature at one or more locations of a plant.

In some embodiments, robotic device 200 includes sensor 250 configured to acquire plant data and inertial navigation device 290 configured to provide a position of robotic device 200. Inertial navigation device 290 may include an accelerometer configured to detect motion, and a gyroscope or multi-axis accelerometer array configured to detect rotation. Reference positions markers may be placed anywhere in an environment surrounding plants 100 and flowers 120 in order to provide the origin for inertial navigation device 290. In some embodiments, the location of a first flower 120 or designated position on plant 100 can serve as the reference point in order to determine the relative or global location of second flower 120. Processing circuit 310 may be configured to store positions of robotic device 200 in any appropriate coordinate system. Processing circuit 310 may be configured to store positions of plants 100 and flowers 120 in the same coordinate system as the positions of robotic device 200 are stored. Robotic device 200 may travel through the environment surrounding plants 100 and flowers 120 in order to update the positions of plants 100 and flowers 120 on an ad hoc or regular basis.

Referring further to FIG. 2A, a robotic device is provided as airborne robotic device 200. Airborne robotic device 200 may include wings 280 coupled to a motor for propulsion. Referring further to FIG. 2B, a robotic device is provided as airborne robotic device 200. Airborne robotic device 200 may include one or more rotors 284 coupled to a motor for propulsion. A motor for propulsion may include an internal combustion engine that provides power by combusting fuel and an oxidant. A motor for propulsion may include an electric motor that draws current from a battery or another electricity source and uses the current to power the electric motor and in turn power the wings 280 or the rotors 284. Airborne robotic device 200 may include a gripping member configured to reversibly attach airborne robotic device 200 to the plant 100 (e.g., while performing a pollination operation to a flower of the plant).

Figure 2C:
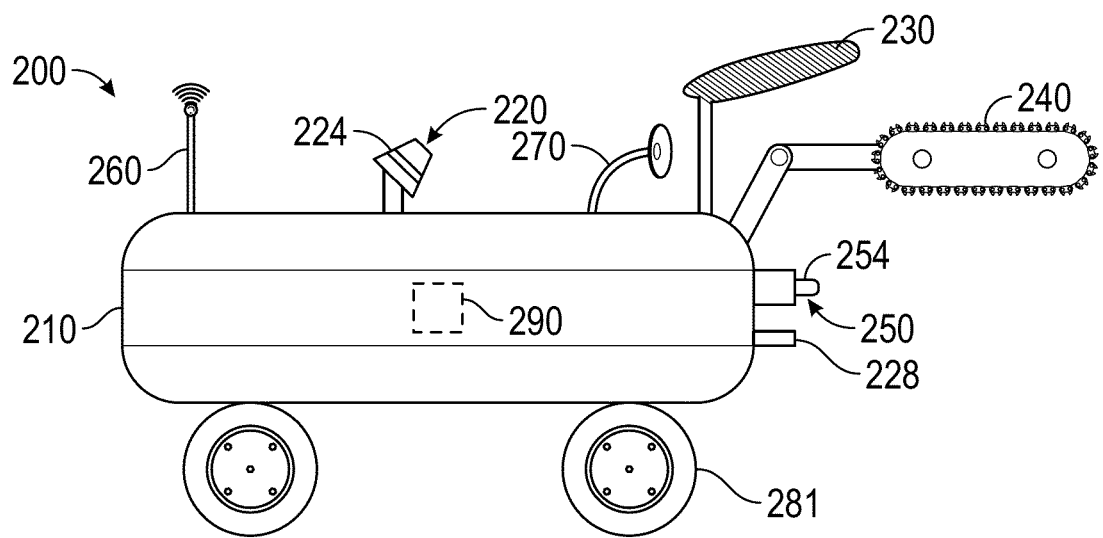
FIGS. 2C and 2D are schematic illustrations of robotic devices according to various alternative embodiments.

Referring to FIG. 2C, a robotic device is provided as ground-based robotic device 200. Ground-based robotic device 200 may include chassis 210, pollination device 220 including nozzle 224, collection device 230, pollination prevention device 240, sensor 250 including camera 254, communication device 260, detection device 270, and inertial navigation device 290. As an alternative to airborne robotic devices 200 shown in FIGS. 2A-2B, ground-based robotic device 200 includes wheels 281 for traversing a landscape. While FIG. 2C shows ground-based robotic device 200 as having wheels 281, ground-based robotic device 201 may include any other device appropriate for ground-based transportation, such as a tread or track, etc. Devices for ground-based transportation such as wheels 281 may be coupled to a motor for propulsion. A motor for propulsion may include an internal combustion engine that provides power by combusting fuel and an oxidant. A motor for propulsion may include an electric motor that draws current from a battery or another electricity source and uses the current to power the electric motor and in turn power the wheels 281, movable legs, or a tread or track, etc. Ground-based robotic device 200 may include a gripping member configured to reversibly attach ground-based robotic device 200 to the plant (e.g., while performing a pollination operation to a flower of the plant).

Figure 2D:
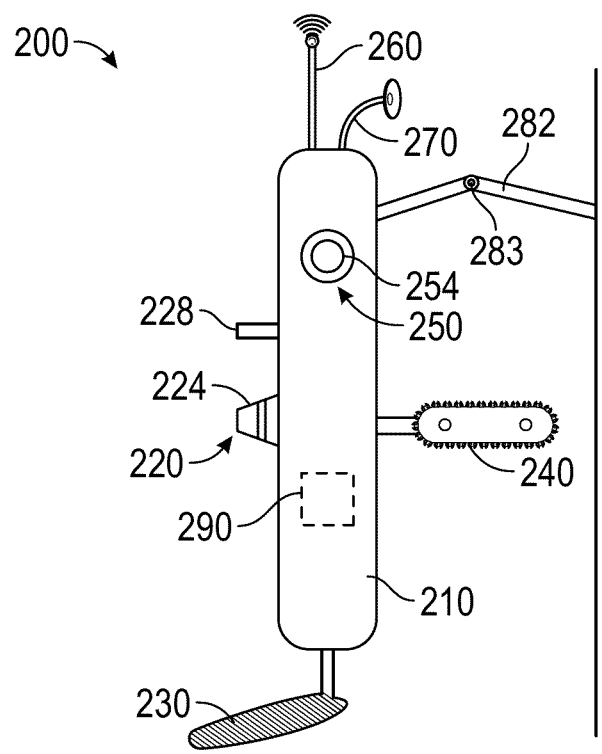

Referring to FIG. 2D, a robotic device is provided as mounted robotic device 200. As shown in FIG. 2D, mounted robotic device 200 is attached to a structure. Mounted robotic device 200 may be reversibly attached to the structure. The structure may be a ceiling, a wall, a floor, a post, etc. The structure may be part of the structure of a greenhouse, and mounted robotic device 200 may be configured to control pollination in the greenhouse. Mounted robotic device 200 may include pollination device 220 including nozzle 224, collection device 230, pollination prevention device 240, sensor 250 including camera 254, communication device 260, detection device 270, and inertial navigation device 290. As an alternative to mobile/roving robotic devices 200 as shown in FIGS. 2A, 2B, and 2C, mounted robotic device 200, being attached to the structure, is generally fixed in at least one point in space. As shown in FIG. 2D, mounted robotic device 200 may include arms 282 and joints 283 in order to change the position of the various components of mounted robotic device 200. Mounted robotic device 200 may be powered by any appropriate power system, such as electricity, a battery, a gas generator, an engine, etc.

Figure 3:
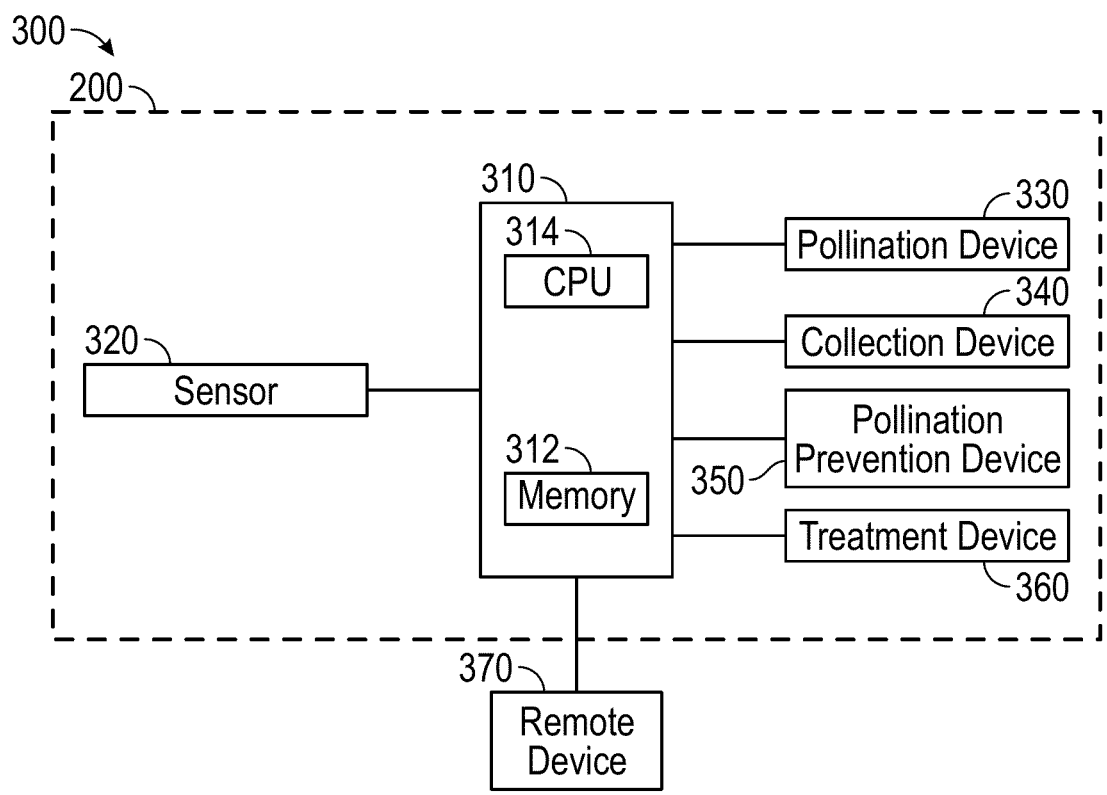
FIG. 3 is a block diagram of a control system for the robotic device of FIG. 1 according to one embodiment.

Referring to FIG. 3, system 300 for pollinating flowers 120 of plants 100 is shown. System 300 includes processing circuit 310 having central processing unit 312 and memory device 314, sensor 320, pollination device 330, collection device 340, pollination prevention device 350, treatment device 360, and remote device 370. Processing circuit 310 is configured to control operation of pollination prevention device 330 to selectively perform a pollination prevention process. In some embodiments, system 300 is implemented on a robotic device such as robotic device 200 (e.g., such that devices including sensor 320, pollination device 330, collection device 340, pollination prevention device 350, treatment device 360, etc., are embodied in robotic device 200). In other embodiments, one or more components of system 300 are implemented remotely from robotic device 200.

Central processing unit 312 may be implemented as a general-purpose processor, an application specific integrated circuit (ASIC), one or more field programmable gate arrays (FPGAs), a digital-signal-processor (DSP), a group of processing components, or other suitable electronic processing components. Memory 314 is one or more devices (e.g., RAM, ROM, Flash Memory, hard disk storage, etc.) for storing data and/or computer code for facilitating the various processes described herein. Memory 314 may be or include non-transient volatile memory or non-volatile memory. Memory 314 may include database components, object code components, script components, or any other type of information structure for supporting the various activities and information structures described herein. Memory 314 may be communicably connected to central processing unit 312 and provide computer code or instructions to central processing unit 312 for executing the processes described herein.

In some embodiments, processing circuit 310 is configured to control operation of at least one of pollination device 330, collection device 340, pollination prevention device 350, and treatment device 360 based on plant data, in order to manage pollination (e.g. pollinating, preventing pollinating, collection pollen 450, etc.) of flower 120 of plant 100. Plant data may include data regarding the species of plant 100. Plant data may include data regarding the size of plant 100 or flower 120, such as height, width, depth, shape, or any relevant geometric measure. Plant data may include data regarding the location of flower 120 (or of multiple flowers 120), such as location relative to the trunk, to a branch, to other flowers 120, or the like. Plant data regarding the size of plant 100 or flower 120 may be based on plant 100 as a single whole structure, or any part of plant 100 such as branches, leaves, or flowers 120. Plant data regarding the size of flower 120 may be based on flower 120 as a single whole structure, or any part of flower 120 (e.g. stigma 410, pistil 420, pollen 450, stamen 430, ovule 440, as shown in FIG. 4C). Plant sensor data may also include data regarding the state of plant 100 or flower 120, such as temperature, surface conductance, moisture content, density, color, intensity of light striking plant 100 or flower 120, or any other plant data. Plant data may be instantaneous in time, or may be a calculated maximum, minimum, median, or mean value, over a period of time.

In some embodiments, plant data includes historical data regarding plant 100 and flower 120. Historical data may include specifications regarding the size of flower 120, such as height, width, depth, shape, or any other relevant geometric measure. The historical data may include specifications for flower 120 as a single whole structure, or for any part of flower 120. Historical data 120 may include data for the growth of flower 120 (e.g., over a season), for the location of its bud, for growth and location of flowers over previous seasons, or the like. The historical data may include at least one image of flower 120.

Plant data may include image data for flower 120 or any part of flower 120. In some embodiments, processing circuit 310 may be configured to determine whether flower 120 has been pollinated or fertilized. For example, plant data may indicate the presence of at least one of previously emplaced pollen 450 on stigma 410, entry of pollen 450 into stigma 410, and a pollen tube. Plant data may indicate whether embryonic development has started. In some embodiments, a user or software program examines image data to determine whether pollination or fertilization has occurred.

In some embodiments, processing circuit 310 is configured to control operation of at least one of pollination device 330, collection device 340, pollination prevention device 350, and treatment device 360 based on environment data regarding an environment surrounding flower 120. The environment surrounding flower 120 may be characterized by any geometry or coordinate system relevant to flower 120. The environment data may be measured or collected by sensor 140. Multiple sensors 140 may be used to collect multiple data points contemporaneously, which may be compared or combined to create a composite impression of the environment surrounding and including flower 120.

The environment data may be received from a source outside the environment, such as user input, a radio weather station, a television weather station, data received via the internet or other online communication sources, or from any other outside source. The environment data may include, but is not limited to: temperature, surface conductance, moisture content, density, color, intensity of light striking flower 120, or any other plant data; atmospheric temperature, dew point, frost point, atmospheric pressure, humidity, or any other data regarding the atmosphere and its moisture content; weather and climate data, such as sunshine, rain, snow, any other form of precipitation, wind, lightning, or any other weather or climate data, or the frequency or expected frequency of any weather or climate event. Environment data may include data concerning a specific instant in time in the past, present, or future, such as a forecast. In some embodiments, the environment data includes at least one of light data regarding an amount of sunlight reaching the environment, moisture data regarding a moisture content of the environment, and obstacle data regarding an obstacle present in the environment.

Remote device 370 may be configured to deliver remote data including a pollination plan to system 300. Remote device 370 may be communicably connected to a remote information source, such as the internet, a local intranet or other local communication protocol, radio, and Bluetooth or other short range communication protocols. A user may provide instructions to system 300 and processing circuit 310 via remote device 370. In some embodiments, remote device 370 is, includes, or is communicably connected to at least one of sensors 140, central computer 130, and central communication hub 132, and may transfer data such as plant data or environment data to system 300 from such devices.

In some embodiments, pollination prevention device 350 is configured to perform at least one of damaging stigma 410 of the flower, removing stigma 410 of flower 120, damaging flower 120, and removing flower 120 from plant 100.

In some embodiments, system 300 includes treatment device 360 configured to apply a treatment to flower 120 after pollination prevention has occurred. The treatment may be a solid, liquid, or gas treatment. Robotic device 200 may include multiple treatments selected to optimally treat various flowers 120 based on the properties of the treatment and of flowers 120 to be treated. Robotic device 200 may mix multiple treatments to provide a composite treatment. Robotic device 200 may mix treatments with a solvent such as water to alter the concentration or consistency of the treatment to be applied. In some embodiments, the treatment includes a medication. In some embodiments, the treatment includes a restorative configured to reverse the prevention of pollination of flower 120. For example, if a water-soluble sealant was used to prevent pollination of flower 120, the treatment may include a water-based wash to wash away the sealant. For example, if a photo-sensitive sealant was used to prevent pollination of flower 120, the treatment may include a delivery of a light flux (e.g., over a specified spectral range) to degrade the sealant.

In some embodiments, plant data includes a pollination plan. A pollination plan may include any set of guidelines, directives, instructions, information, describing the timing of pollination of flowers 120, status of pollination and status of and fertilization of flowers 120, pollen type of pollen 450 to be applied for pollination, etc. A status may be a binary indication of whether flowers 120 are pollinated or fertilized. A status may be a value on a spectrum of pollination or fertilization, or a subjective indicator of relative pollination or fertilization. A status may indicate the presence of previously emplaced pollen 450 on stigma 410; entry of pollen 450 into stigma 410; a pollen tube; or whether embryonic development has started. Processing circuit 310 may be configured to update the pollination plan based on a status. For example, if a status indicates flower 120 of plant 100 has been pollinated, then the pollination plan may avoid any future pollination of flower 120.

A pollination plan may include directions to apply pollen 450 (see FIG. 4C) of a specific pollen type to first flower 120 of plant 100, and pollen 450 of a different pollen type to second flower 120 of plant 100. A pollen type may be any characteristic associated with pollen 450. For example, a pollen type could describe characteristics of pollen 450 such as height, width, depth, volume, mass, density, color, surface roughness, hardness, longevity, response to temperature or moisture changes, genetic information including relationship to other plants 100 and pollen 450, or any other such characteristics.

A pollination plan may include directions to modify pollination based on self-pollination goals, cross-pollination goals, harvesting goals, target fruits, or any other such factor. Based on the pollination plan, pollen 450 may be delivered to selected second flower 120 after collection from first flower 120. A pollination plan may include an identification of which flowers 120 or plants 100 the plan should be applied to. In some embodiments, this identification is specific, while in some embodiments it is cumulative, e.g., specifying a number of flowers 120, a fraction of flowers 120, a number of plants 100, or a fraction of plants 100 for which the plan is (or is not) to be applied to. A pollination plan may include a database of flowers 120, plants 100, pollens 450, and environments surrounding flowers 120, plants 100, and pollens 450. The database may store information such as the position of items stored in the database. A pollination plan may include travel routes amongst flowers 120 and plants 100 to optimally guide robotic device 200 through their pollination and collection tasks. In some embodiments, a pollination plan includes a status for flower 120 or at least one flower 120 of a plurality of flowers 120 indicating whether at least one flower 120 is available for pollination, and a location for at least one flower 120. In some embodiments, the performing of the pollination plan is monitored (e.g., by onboard sensors such as cameras) and documented. This documentation can be stored on-board, or can be reported to a remote entity. In some embodiments, the success (or lack of it) in performing aspects of the pollination plan can be used as feedback information for subsequent pollination plans or actions.

In some embodiments, a pollination plan includes a timing, or an adjustment to the timing of pollination of flower 120. For example, flower 120 may have the timing of pollination advanced or delayed in order to maximize exposure to pro-growth factors such as sunlight, rain, fertilizer, and soil nutrients. In some embodiments, the timing of pollination of flower 120 may be adjusted to align with pollinating other flowers 120, so that all flowers 120 receiving pollen 450 of the same pollen type may be pollinated at the same time with same pollen 450. In some embodiments, a pollination plan includes an adjustment to timing of pollination of at least one of a plurality of flowers 120.

In some embodiments, a pollination timing for flower 120 falls within a predetermined pollination window. For example, a pollination timing may fall within a period having sunlight; a period lacking sunlight; a period corresponding to a pollination window for other flowers 120 (e.g. for at least one of a plurality of flowers 120); a period based on seasonal or climate schedules; a period based on monthly, annual, or seasonal calendars; or any other period. A pollination window may be of varying lengths of time; if robotic device 200 is not able to perform a pollination task during a predetermined pollination window, the pollination window may be advanced to a future period.

In some embodiments, a pollination timing is based on the readiness of at least one flower 120 to being fertilized. For example, processing circuit 310 may be configured to determine whether flower 120 has matured sufficiently for being pollinated; processing circuit 310 may be configured to recognize when a minimum amount of time has passed since a previous pollination.

In some embodiments, processing circuit 310 is configured to estimate a development time for a fruit based on a pollen type associated with the fruit, and then to determine the pollination timing for at least one flower 120 based on the development time for the fruit. For example, processing circuit 310 may use a growth model for growth of a fruit to calculate the development time required for the fruit to develop, compare the development time to a target time for when the fruit is expected to be harvested, and set the pollination timing accordingly.

A growth model for plant 100 or portions of plant 100 such as flowers 120, fruits, seeds, etc. may include various factors including but not limited to instantaneous sunlight intensity, total sun exposure over a relevant time period, temperature, humidity, rainfall, time of year, proximity of other plants 100 or portions of plants 100, growth characteristics of other plants 100 and or portions of plants 100, desired growth for other plants 100 or portions of plants 100, potential future growth of plant 100 or portions of plant 100, the growth response of plant 100 or portions of plant 100 to being pollinated or fertilized, and any user input regarding desired growth characteristics. The growth model could demonstrate a linear response, a power law response, an exponential response, a sinusoidal response, or any other relationship to any factor. For example, a growth model could predict that plant 100 or portions of plant 100 will grow in the presence of greater than a minimum value of each factor, but the minimum value for each factor also increases as plant 100 or portions of plant 100 grow, such that plant 100 or portions of plant 100 eventually reach a steady state size.

In some embodiments, the pollination timing for at least one flower 120 is determined such that at least one fruit grown by plant 100 is ready to be harvested within a predetermined harvesting window. A harvesting window may be any period of time for harvesting fruit. For example, a harvesting window could correspond to a single predetermined period of time; a harvesting window could be determined based on monthly, seasonal, annual, commercial, or other regular schedules.

In some embodiments, a pollination plan includes a timing, or an adjustment to the timing of collecting pollen 450 from flower 120. For example, timing of collecting pollen 450 from flower 120 may be advanced or delayed in order to more efficiently gather pollen 450 from multiple flowers 120 and plants 100, such as by collecting pollen 450 of the same pollen type from multiple flowers 120. In some embodiments, a pollination plan includes an amount of pollen to be collected from a plant or flower.

In some embodiments, a pollination plan includes a load-bearing capacity for a site associated with at least one of a plurality of flowers 120. The load-bearing capacity may include capacity for bearing weight, volume, specific fruits or classes of fruit, or any other load. The load-bearing capacity may include factors such as historical data, plant data, and environment data.

In some embodiments, a pollination plan includes a nutrient supplying capacity for a site associated with at least one of a plurality of flowers 120. The nutrient-supplying capacity may be based on factors such as historical data for the plant, distance to roots or other portions of plant 100, soil nutrients and fertilizer, access to sunlight and rain, environment data, other plant data, proximity to other plants 100 and features or portions of plants 100, etc.

In some embodiments, processing circuit 310 is configured to monitor whether a fertilization of at least one flower 120 occurred within a predetermined pollination time frame after a first pollination, and processing circuit 310 is configured to apply a second pollination to at least one flower 120 based on whether fertilization of at least one flower 120 occurred. For example, processing circuit 310 may be configured to control operation of detection device 270 to detect embryonic development, report a status of fertilization for at least one flower 120, and direct pollination device 220 to pollinate at least one flower 120 if fertilization has not occurred within the predetermined pollination time frame.

In some embodiments, the second pollination includes pollen 450 of a different pollen type than the pollen type of the first pollination. Characteristics of the first and second pollen types may be used to determine which pollen type should be used for the second pollination. For example, a pollen type may include information regarding an affinity for the pollen type to specific flower 120; the second pollination may be performed using pollen 450 with a pollen type of a lesser or greater affinity for flower 120 than pollen 450 of the first pollination. In some embodiments, the second pollination includes pollen 450 of the same pollen type as the pollen type of the first pollination.

Figure 4A:
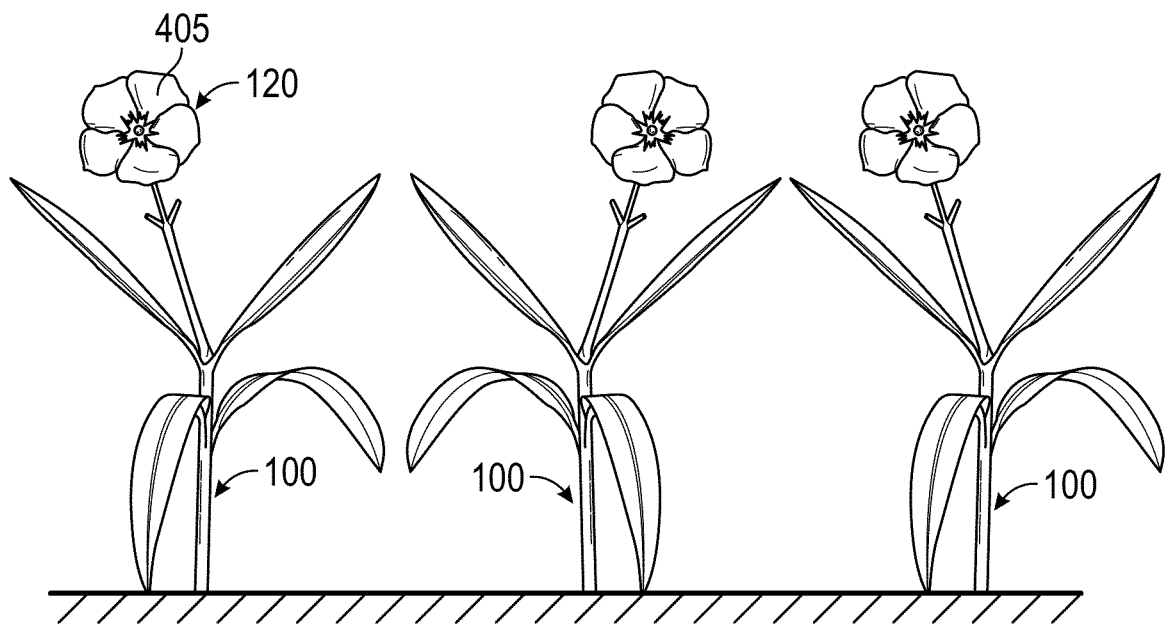
FIGS. 4A-4C illustrate various portions of a plant for pollination according to various embodiments.
Figure 4B:
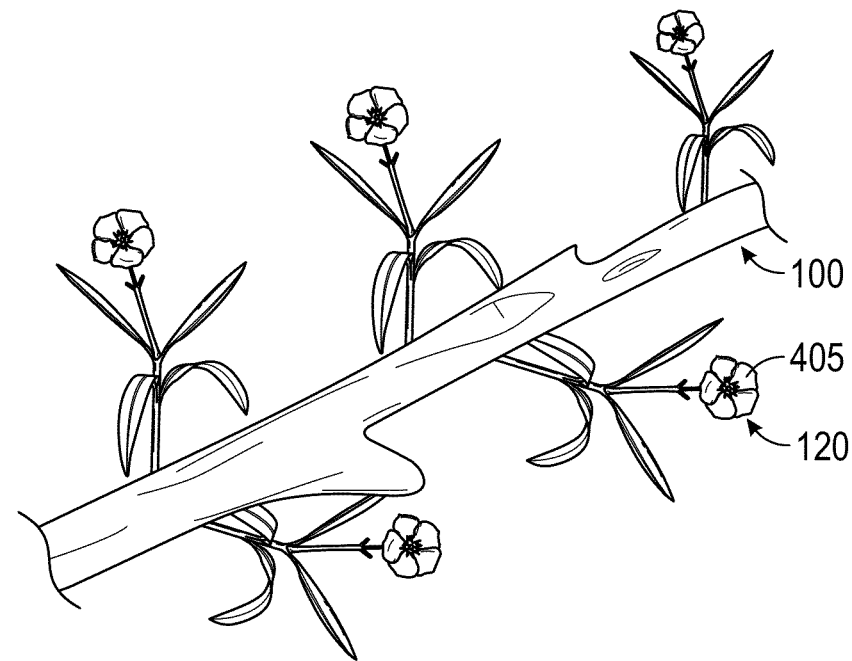
Figure 4C:
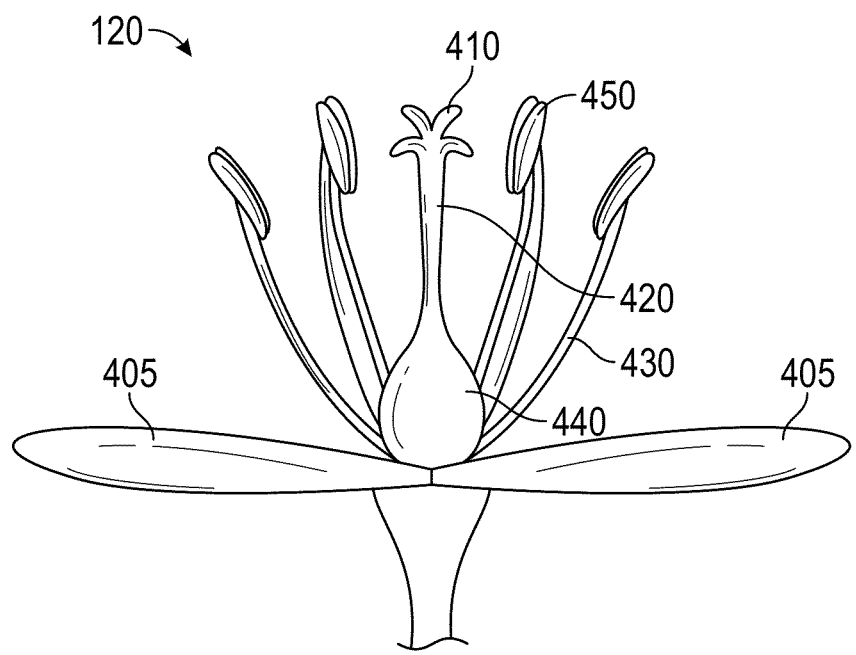

Referring to FIGS. 4A-4C, various plants 100 and flowers 120 are shown in greater detail. Referring further to FIGS. 4A-4B, plants 100 are shown, having flowers 120 with petals 405.

Referring further to FIG. 4C, flower 120 is shown with portions including petals 405, stigma 410, pistil 420, stamen 430, ovule 440, and pollen 450. In some embodiments, sensors such as sensor 140 and sensor 250, and detection devices such as detection device 270, are configured to acquire plant data regarding plants 100 and flowers 120, as well as portions of flowers 120.

Figure 5:
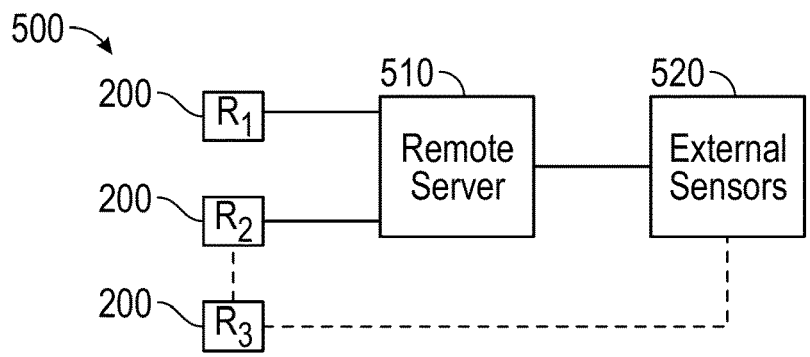
FIG. 5 is a block diagram of a communication network including a plurality of robotic devices according to one embodiment.

Referring to FIG. 5, a communication scheme 500 is shown for a plurality of robotic devices 200, along with remote server 510, and external sensors 520. Communication may take place via any of a variety of communication protocols, including but not limited to signals throughout the electromagnetic spectrum (e.g. infrared, radio frequency, microwave signals, etc.) and electronic communication protocols such as wireless internet, wired internet, Bluetooth, and near field technologies.

In some embodiments, external sensors 520 acquire plant data regarding plants 100 and flowers 120 and environment data regarding an environment surrounding plants 100 and flowers 120. Remote server 510 may receive the plant data and environment data, implement a pollination plan based on the plant data and environment data, and transmit the pollination plan to the plurality of robotic devices 200. First robotic device 200 may communicate with second robotic device 200 to divide pollination tasks within the environment, such that first robotic device 200 completes all pollination tasks within a first global range, and second robotic device completes all pollination tasks within a second global range.

In some embodiments, a user creates a pollination plan, and uses remote server 510 to transmit the pollination plan to robotic device 200. External sensors 520 may acquire plant data regarding plants 100 and flowers 120 and environment data regarding an environment surrounding plants 100 and flowers 120. The user may interpret the plant data and environment data in order to modify the pollination plan.

In some embodiments, processing circuit 310 is configured to control operation of robotic device 200 to selectively perform a pollination prevention process to at least temporarily prevent pollination of flower 120 based on the plant data. In some embodiments, pollination is prevented by blocking stigma 410 of flower 120. In other embodiments, pollination is prevented by at least one of damaging stigma 410, removing stigma 410, damaging flower 120, and removing flower 120.

Referring to FIGS. 6A-6E, in some embodiments, processing circuit 310 may be configured to control operation of devices such as removal device 240 and pollination prevention device 330 in order to prevent pollination of flower 120. Removal device 240 and pollination prevention device 330 may include at least one of cutting device 610, photodamage device 620, chemical device 630, and thermal device 640.

Figure 6A:
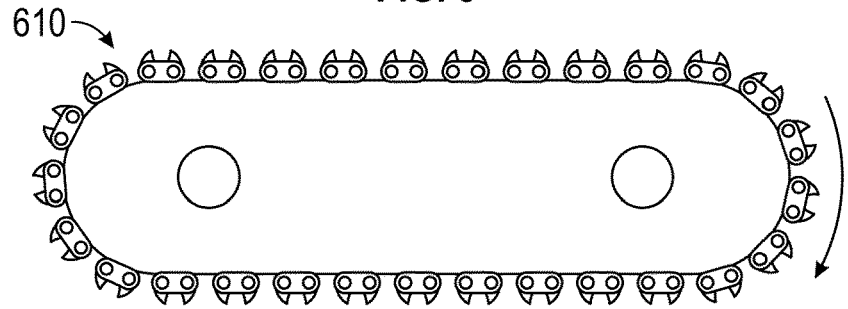
FIGS. 6A-6E illustrate various pollination prevention devices usable in connection with the robotic devices of FIG. 1 according to various embodiments.

Referring to FIG. 6A, in one embodiment, cutting device 610 is a chain saw. Cutting device 610 may also be a saw, a knife, a circular saw, or any other cutting device; it may be made of plastic, metal, a metal alloy, or any other material.

Figure 6B:
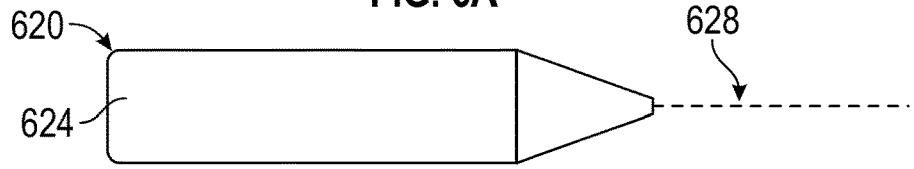

Referring to FIG. 6B, in one embodiment, photodamage device 620 includes laser device 624. Laser device 624 may include a motion control system and computer numerical control to direct the direction, intensity, and other properties of laser 628 generated by laser device 624 according to a predetermined pattern, user input, feedback from processing circuit 310, or any other control input. In some embodiments, laser device 624 includes multiple lasers 628 directed in multiple directions to prevent pollination of flower 120 from multiple directions.

In some embodiments, photodamage device 620 generates infrared light, ultraviolet light, or other light configured to affect plant 100, flower 120, or stigma 410 of flower 120. For example, photodamage device 620 may generate light that interferes with photosynthesis processes taking place in plant 100.

Figure 6C:
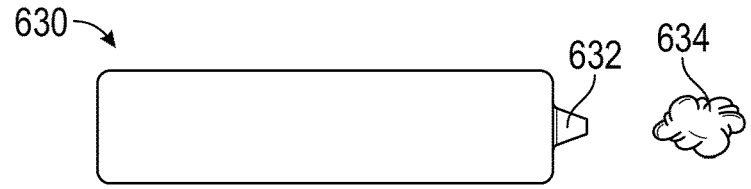

Referring to FIG. 6C, in some embodiments, chemical device 630 applies chemicals 634 to plant 100, or a portion of plant 100 such as flower 120 or stigma 410, in the form of a solid, a liquid, a gas, or a combination thereof. Chemical device 630 may modify the properties of chemicals 634 before applying chemicals 634 to flower 120, such as the temperature or concentration of chemicals 634. Chemical device 630 may include a supply of solvent, such as water or ethanol, to modify the concentration of chemicals 634. Chemical device 630 may include spray nozzle 632 and may apply chemicals 634 to flower 120 as a spray. Chemical device 630 may mix chemicals 634 with a solvent, or with other chemicals 634, before applying chemicals 634 to flower 120. Chemical device 630 may contain multiple chemicals 634 configured to prevent pollination of multiple flowers 120, and processing circuit 310 may be configured to selectively control operation of chemical device 630 to apply chemicals 634 preferentially selected for a specific plant 100 or flower 120. The flow rate of chemicals 634 leaving chemical device 630 may be modulated in various ways, including but not limited to being held constant, increased and decreased according to a pattern, and being modulated in response to feedback from processing circuit 310, user input, or any other chemical control.

In some embodiments, chemicals 634 include a sealant to seal (e.g., to block pollen access through) stigma 410 of flower 120. The sealant may be a glue. The sealant may be water-soluble or waterproof. The sealant may be configured to degrade over the lifespan of flower 120. The sealant may be configured to degrade after a specified time period (e.g., days or weeks) thereby acting to delay pollination only for the specified time period. The degradation rate may be based upon temperature, moisture, photosensitivity, characteristics of the sealant, etc. The sealant may be configured to be selectively removable (e.g., by later application of a chemical or light to degrade it). The sealant may be configured to divert a bee from approaching flower 120. For example, the sealant may include a pheromone that directs a bee to avoid flower 120.

Figure 6D:
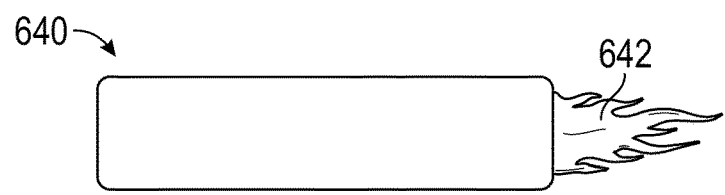

Referring to FIG. 6D, in one embodiment, thermal device 640 is a combustion-based heat source, and provides flame 642. The combustion fuel may be a solid, a liquid, or a gas. The properties of flame 642, such as its temperature, length, or whether it is laminar or turbulent, may be controlled by, for example, regulating flow rates of an oxidizer and the fuel. Flame 642 may be premixed or may be a diffusion flame. Flame 642 may be continuous or intermittent. The properties of flame 642 may be held constant, or may be modulated or increased or decreased according to a pattern, feedback from processing circuit 310, user input, or any other control.

Figure 6E:
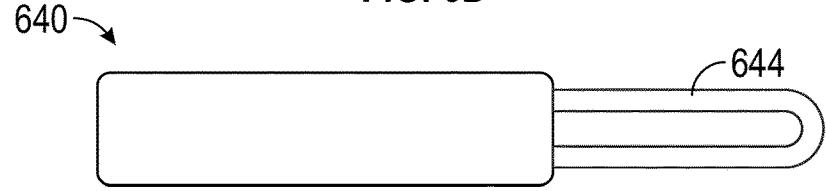

Referring to FIG. 6E, in some embodiments, thermal device 640 includes heated element 644. Heated element 644 may include any material configured to store and release focused heat, including but not limited to a metal, a metal alloy, or a carbon-based structure. Heated element 644 may have a solid surface, or may have teeth, serrations, or other structures configured to facilitate damaging or removing flowers 120 or stigma 410. Heat may be transferred to heated element 644 by a combustion process, or by an electrical resistor, or any other heating process. The temperature of heated element 644 may be modulated, may be held constant, or may be increased and decreased according to a pattern, feedback from processing circuit 310, user input, or any other temperature control.

As shown in FIGS. 2A-2D, in some embodiments, robotic device 200 includes a marking device 228 configured to apply a marker to flower 120 or to plant 100 in the vicinity of flower 120 to indicate that flower 120 has been pollinated. The marker may be a visual marker, such as a chemical, dye, or ink visible in the visual spectrum. The marker may also be a chemical, dye, ink, or other material visible in other portions of the electromagnetic spectrum. The marker may be fluorescent. The marker may be a radio-frequency identifier. The marker may include a radio label or an isotopic marker. The marker may be configured to emit an audio signal, or a chemical signal. The marker may be configured to decrease in signal intensity over time.

In some embodiments, processing circuit 310 is configured to determine whether plant 120 has been pollinated. Processing circuit 310 may analyze plant data to determine the presence of previously emplaced pollen 450 on stigma 410, entry of pollen 450 into stigma 410, or a pollen tube. In some embodiments, processing circuit 310 may be configured to determine whether plant 100 has been fertilized, e.g. if embryonic development has started.

In some embodiments, processing circuit 310 is configured to estimate at least one of a seed production amount and a fruit production amount for plant 100 based on the plant data including a status indicating whether plant 100 has been pollinated or whether plant 100 has been fertilized. Growth models for seed production and fruit production may support estimating seed production and fruit production. Growth models for seed production and fruit production may reflect how many of a plurality of flowers 120 of plant 100 have been pollinated, and how many of a plurality of flowers 120 of plant 100 have been fertilized. Growth models for seed production and fruit production may reflect the access to nutrition, soil nutrients, fertilizer, sunlight, and rain of plant 100; and the positions of flowers 120 on plant 100 relative to each other and to other portions of plant 100 such as roots and outer branches.

In some embodiments, processing circuit 310 is configured to determine a status for at least one flower 120, and update the pollination timing for another flower 120 of the plurality of flowers 120 of plant 100 based on the status. For example, if first flower 120 has not been successfully pollinated after multiple attempts, processing circuit may be configured to update the pollination plan to advance the pollination timing of second flower 120 of plant 100 in order to encourage pollination of more flowers 120 of plant 100.

Figure 7:
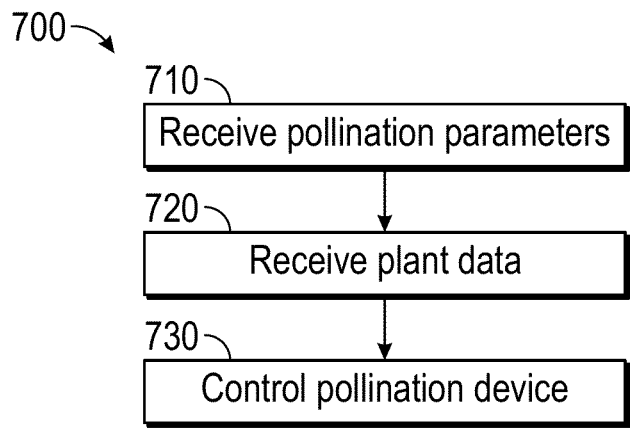
FIG. 7 is a block diagram of a method of pollinating plants according to one embodiment.

Referring to FIG. 7, method 700 is shown for pollinating plant 100 using a pollination plan. At 710, pollination parameters, e.g., a pollination plan, are received. Pollination parameters, such as a pollination plan, may include any information for selectively pollinating flower 120 or at least one flower 120 of a plurality of flowers 120. At 720, plant data is received. Plant data may be acquired by sensors such as sensor 140 and sensor 250, and may include data regarding physical characteristics of plant 100 and flowers 120, data regarding the state of plant 100 and flowers 120, data regarding a pollination status or a fertilization status of flowers 120, historical data, and image data, among other data. At 730, processing circuit 310 controls operation of robotic device 200 to pollinate flower 120 of plant 100 based on the pollination plan and the plant data.

Figure 8:
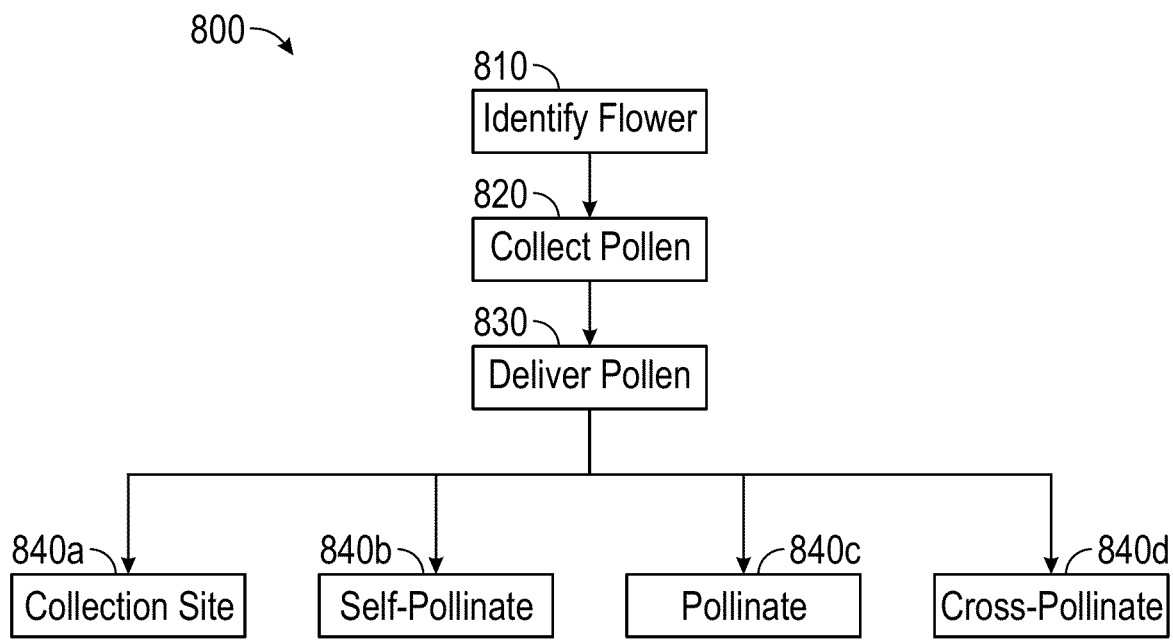
FIG. 8 is a block diagram of a method of pollinating plants according to another embodiment.

Referring to FIG. 8, method 800 is shown for collecting and delivering pollen 450 from flower 120. At 810, flower 120 is identified for collection of pollen 450. Flower 120 may be identified based on characteristics of flower 120 such as species, size, location; based on information from a pollination plan; based on a status such as a indicating whether flower 120 is pollinated or whether flower 120 is fertilized; or based on any other factor. At 820, pollen 450 is collected. For example, processing circuit 310 may be configured to control operation of collection device 230 to collect pollen 450 from flower 120.

At 830, pollen 450 is delivered. Processing circuit 310 may be configured to control operation of robotic device 200 to deliver pollen to a collection site (840*a*). A self-pollination may be performed by pollinating flower 120 with pollen 450 collected from same flower 120 (840*b*). A pollination may be performed by pollinating another flower 120 of plant 100 of the same species as flower 120 from which pollen 450 was collected (840*c*). A cross-pollination may be performed by pollinating flower 120 of a different species than flower 120 from which pollen 450 was collected (840*d*).

Figure 9:
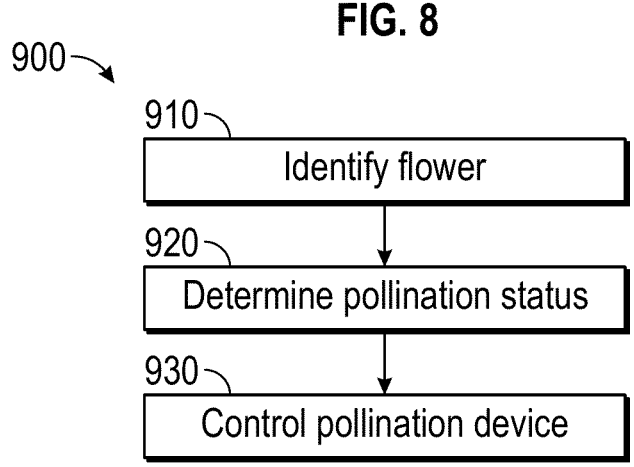
FIG. 9 is a block diagram of a method of pollinating plants according to another embodiment.

Referring to FIG. 9, method 900 for monitoring and pollinating plants 100 is shown. At 910, flower 120 is identified for pollination. Flower 120 may be identified based on a pollination plan. Flower 120 may be identified based on a previous pollination. Flower 120 may be identified based on visual characteristics of flower 120 or plant 100 having flower 120. At 920, the status of pollination of flower 120 is determined A detection device 270 may be configured to detect at least one of previously emplaced pollen 450 on stigma 410, entry of pollen 450 into stigma 410, and a pollen tube. Detection device 270 may also be configured to detect if fertilization has occurred, e.g. if embryonic development has occurred. At 930, processing circuit 310 is configured to control operation of pollination device 220 to apply pollen 450 to stigma 410 based on whether flower 120 is pollinated or whether flower 120 is fertilized.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A robotic device for collecting pollen from plants, comprising:
   a collection device;
   a sensor configured to acquire plant data regarding a plant; and
   a processing circuit storing a pollination plan indicating a status of whether a flower of the plant is pollinated or whether the flower is fertilized, the processing circuit configured to identify the flower of the plant for collection of pollen based on the status and control operation of the collection device to collect pollen from the flower of the plant based on the plant data and the status.

2. The robotic device of claim 1, wherein the plant data includes a location of at least one of the flower and the plant.

3. The robotic device of claim 1, wherein the plant data includes a species of the plant.

4. The robotic device of claim 1, wherein the plant data includes historical data regarding the plant.

5. The robotic device of claim 1, further comprising a sensor configured to collect environment data regarding an environment surrounding the plant.

6. The robotic device of claim 1, wherein the processing circuit is configured to further control operation of the collection device to deposit the pollen in a collection site.

7. The robotic device of claim 1, wherein the collection device includes a moist surface.

8. The robotic device of claim 1, wherein the collection device includes an adhesive surface.

9. The robotic device of claim 1, wherein the processing circuit is configured to further control operation of the collection device to deliver the pollen to a second flower.

10. The robotic device of claim 1, wherein the robotic device is airborne.

* * * * *